(12) United States Patent
Katz et al.

(10) Patent No.: US 7,932,084 B2
(45) Date of Patent: Apr. 26, 2011

(54) METHODS AND COMPOSITIONS FOR GROWING ADIPOSE STEM CELLS

(75) Inventors: Adam J. Katz, Charlottesville, VA (US); Anna M. Parker, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 129 days.

(21) Appl. No.: 12/066,348

(22) PCT Filed: Sep. 8, 2006

(86) PCT No.: PCT/US2006/034915
§ 371 (c)(1),
(2), (4) Date: Mar. 19, 2008

(87) PCT Pub. No.: WO2007/030652
PCT Pub. Date: Mar. 15, 2007

(65) Prior Publication Data
US 2008/0248003 A1    Oct. 9, 2008

Related U.S. Application Data

(60) Provisional application No. 60/715,025, filed on Sep. 8, 2005, provisional application No. 60/716,337, filed on Sep. 12, 2005.

(51) Int. Cl.
*C12N 5/00* (2006.01)
*C12N 15/00* (2006.01)
(52) U.S. Cl. ........................ 435/325; 435/455
(58) Field of Classification Search .................. 435/325, 435/455
See application file for complete search history.

(56) References Cited

U.S. PATENT DOCUMENTS

| | | | | |
|---|---|---|---|---|
| 5,286,716 | A * | 2/1994 | Risau et al. | 514/21 |
| 5,612,029 | A * | 3/1997 | Bennett et al. | 424/94.64 |
| 7,470,537 | B2 * | 12/2008 | Hedrick et al. | 435/325 |
| 7,514,075 | B2 * | 4/2009 | Hedrick et al. | 424/93.7 |
| 2006/0182724 | A1 * | 8/2006 | Riordan | 424/93.7 |

* cited by examiner

*Primary Examiner* — Michael C. Wilson
(74) *Attorney, Agent, or Firm* — Schwegman, Lundberg & Woessner, P.A.

(57) ABSTRACT

The present invention relates to adipose tissue-derived stem cells and to methods and compositions for enhancing growth and differentiation of such cells. The invention further relates to growing such cells in serum-free or low serum growth medium, and formulations thereof.

17 Claims, 4 Drawing Sheets

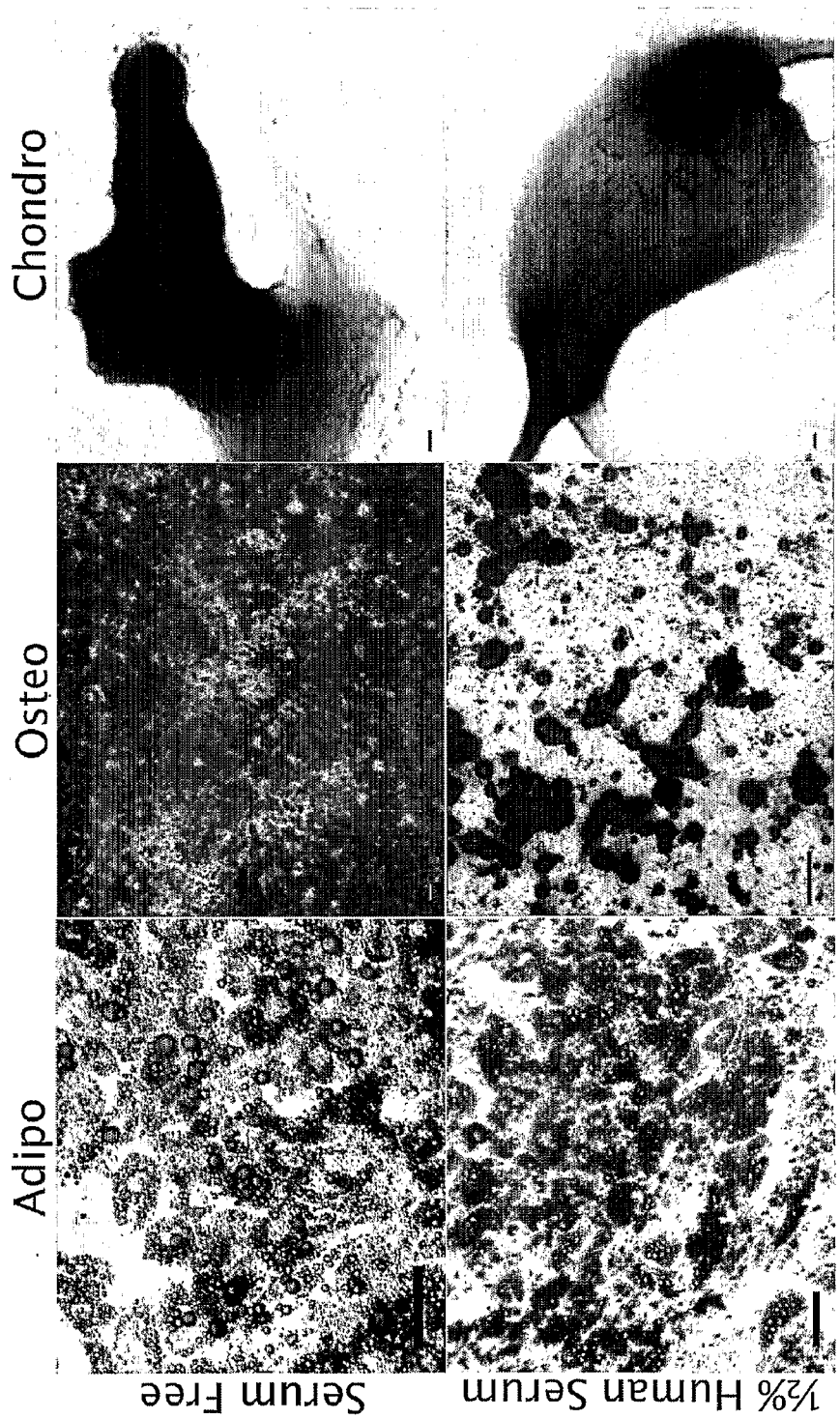

US 7,932,084 B2

METHODS AND COMPOSITIONS FOR GROWING ADIPOSE STEM CELLS

CROSS REFERENCE TO RELATED APPLICATIONS

This application is a national stage filing of International Application No. PCT/US2006/034915, filed on Sep. 8, 2006, which claims priority under 35 U.S.C. §119(e) to U.S. Provisional Application Ser. Nos. 60/715,025 filed Sep. 8, 2005, and 60/716,337, filed Sep. 12, 2005, the disclosures of which are incorporated by reference in their entirety herein.

US GOVERNMENT RIGHTS

This invention was made with United States Government support under National Institutes of Health Grant No. R21 HL72141-01. The United States Government therefore has certain rights in the invention.

FIELD OF THE INVENTION

The present invention relates to the field of stem cell culture media and to methods for culturing such cells. The present invention relates generally to adipose stem cells and to methods of growing and inducing differentiation of adipose stem cells. More particularly, the present invention provides methods and materials for culturing adipose tissue-derived stem cells in a substantially undifferentiated state with and without a feeder layer using a defined serum-free or low serum medium. The present invention has applications in the areas of cell culture, tissue transplantation, drug discovery, and gene therapy.

BACKGROUND

Advancements in stem cell research now suggest potential applications ranging from bone [1-3] and cartilage [4] repair, to the treatment of heart attacks [5-7] and strokes [8,9]. With this ever-broadening array of promising therapies, the use of animal products in stem cell culture emerges as a common hurdle. Significant cell expansion in vitro has typically relied on media supplemented with largely uncharacterized animal sera. The clinical use of cells exposed to such sera presents numerous safety issues. Xenogeneic antigens introduced in this way are internalized by cells in culture and cannot be eliminated despite multiple washes in buffered saline solutions [10]. These foreign antigens have been known to trigger significant immune reactions clinically. Human cells cultured in fetal calf serum ("FCS"), and subsequently transplanted into patients have induced severe anaphylaxis [11], and arthus-like immune reactions consistent with type III hypersensitivity reactions [12]. Additional reports of the sustained elevation of anti-FCS antibodies indicate a maintained sensitively to cells exposed to FCS. This unintended "vaccination" against the transplanted cells expressing FCS antigens may be partly responsible for the decreased durability observed with in gene therapy trials, particularly when multiple doses of FCS cultured cells are given [13]. The elimination of this undefined and potentially dangerous component in cell culture media would reduce the exposure of patients to xenogeneic pathogens and allow for multiple cell administrations without the risk of a stimulated immune response or in the worst case, anaphylaxis.

Mesenchymal stem cells in general, and adipose stem cells in particular, hold great promise for future clinical therapies which enhance the body's natural ability to heal itself. One hurdle common to the use of these potential therapies is the current practice of using fetal bovine serum or other animal sera in the culture media of cells intended for use in humans. The undefined and variable nature of animal sera, as well as the associated risk of introducing xenobiotic pathogens and triggering severe allergic responses in some subjects, presents a technical problem presently unresolved in the field.

In recent years, the identification of mesenchymal stem cells, chiefly obtained from bone marrow, has led to advances in tissue regrowth and differentiation. Such cells are pluripotent cells found in bone marrow and periosteum, and they are capable of differentiating into various mesenchymal or connective tissues. For example, such bone-marrow derived stem cells can be induced to develop into myocytes upon exposure to agents such as 5-azacytidine (Wakitani et al., Muscle Nerve, 18 (12), 1417-26 (1995)). It has been suggested that such cells are useful for repair of tissues such as cartilage, fat, and bone (see, e.g., U.S. Pat. Nos. 5,908,784, 5,906,934, 5,827,740, 5,827,735), and that they also have applications through genetic modification (see, e.g., U.S. Pat. No. 5,591,625). While the identification of such cells has led to advances in tissue regrowth and differentiation, the use of such cells is hampered by several technical hurdles. One drawback to the use of such cells is that they are very rare (representing as few as ½,000,000 cells), making any process for obtaining and isolating them difficult and costly. Of course, bone marrow harvest is universally painful to the donor. Moreover, such cells are difficult to culture without inducing differentiation, unless specifically screened sera lots are used, adding further cost and labor to the use of such stem cells. U.S. Pat. No. 6,200,606 by Peterson et al., describes the isolation of CD34+ bone or cartilage precursor cells (of mesodermal origin) from tissues, including adipose.

The presence of adult multipotent "stem" cells has been demonstrated in a large number of tissues, for example the bone marrow, blood, liver, muscle, the nervous system, and in adipose tissue. Adult "stem" cells, which in theory are capable of infinite self-renewal, have great cell plasticity, i.e. the ability to differentiate into tissues other than those for which it was believed they were destined. The properties of said cells, which are similar to those of embryonic stem cells (ES), open up considerable therapeutic perspectives especially as their use does not pose the problems of compatibility and ethics, encountered with ES cells.

Adipose tissue plays an important and overlooked role in the normal development and physiology of humans and other mammalian species. Many different kinds of fat exist. The most common type is white adipose tissue, located under the skin (subcutaneous fat), within the abdominal cavity (visceral fat) and around the reproductive organs (gonadal fat). Less common in the adult human is brown adipose tissue, which plays an important role in generating heat during the neonatal period; this type of fat is located between the shoulder blades (interscapular), around the major vessels and heart (periaortic and pericardial), and above the kidney (suprarenal).

As women mature, they develop increased amounts of mammary adipose tissue. The mammary fat pad serves as an energy source during periods of lactation. Indeed, reproductive capacity and maturation are closely linked to the adipose tissue stores of the individual. Puberty in women and men correlates closely with the production and release of leptin, an adipose tissue derived hormone, and to body fat composition. Other adipose tissue sites play a structural role in the body. For example, the mechanical fat pads in the soles of the feet provide a cushion against the impact of walking. Loss of this fat depot leads to progressive musculoskeletal damage and impaired mobility. Bone marrow fat cells are present in bone marrow to provide energy to developing blood cells within the marrow. Bone marrow adipocytes are different than adipocytes present in adipose tissue, differing in morphology, physiology, biochemistry as well as their response to various stimulators such as insulin. Adipocytes present in bone marrow stroma may function to: 1) regulate the volume of hemodynamically active marrow; 2) serve as a reservoir for lipids needed in marrow cell proliferation, and 3) may be developmentally related to other cell lineages such as osteoblasts. White adipose tissue (i.e. body fat) in contrast, is involved in lipid metabolism and energy homeostasis (Gimble, The New Biologist 2(4), 1990, pp. 304-312).

There is a long felt need in the art for methods to identify, select, grow, and induce differentiation of adipose tissue-derived stem cells. The present invention satisfies these needs.

SUMMARY OF THE INVENTION

The present invention provides methods and compositions to grow and differentiate adipose stem cell subpopulations in a serum-free medium. The present invention further provides methods and compositions to grow and differentiate adipose stem cell subpopulations in a low serum medium. The present invention is useful for the expansion of primary cells or cell lines in culture.

The present application further provides a new growth medium formulation for the expansion of adipose stem cell populations. Unexpectedly, in one aspect, a defined medium is provided which is serum-free. In one aspect, the medium requires only 0.5% serum enrichment, an amount easily obtained with a small blood draw. In one aspect, the serum is human. The new medium formulation of the present invention allows for the expansion of cells at rates significantly above those possible using present methods. Furthermore, the high growth rate achieved with the medium formulation of the present invention allows for the harvest of sufficient cell numbers for use in trials without the need for first obtaining large tissue samples.

In another embodiment, the invention provides a new medium formulation and method for the culture of adipose stem cells in a completely serum-free environment. This serum-free medium allows for the study of cells in a completely chemically defined environment, as well as the use of the cells in human trials without the risks associated with animal sera.

In one embodiment, a cell culture medium for growing adipose tissue-derived stem cells in an undifferentiated state or in a substantially undifferentiated state is provided which includes a low osmotic pressure, low endotoxin basic medium that is effective to support the growth of stem cells. In one aspect, the cells are adipose-tissue derived stem cells.

In one embodiment, the medium is combined with a nutrient serum effective to support the growth of stem cells and a substrate selected from the group consisting of feeder cells and an extracellular matrix component derived from feeder cells. One of ordinary skill in the art will appreciate that adhesion factors other than extracellular matrix components can be used as well. In another aspect, no feeder layer is provided. In yet another aspect, no extracellular matrix component is provided. In yet another aspect, conditioned medium can be used to supplement the growth medium of the invention. In one aspect, the conditioned medium is serum-free.

In one embodiment, the medium further includes, but is not limited to, non-essential amino acids, an anti-oxidant, and at least one first growth factor.

In one aspect, the invention is useful for clinical trials. The present invention is useful because no special pathogen testing is required for non-human serum. In one aspect, no serum is used.

In one embodiment, adipose tissue cells are isolated in the presence of serum-containing medium. In another embodiment, adipose tissue cells are isolated in the presence of medium with serum.

In one embodiment, the present invention provides a novel medium which is useful for inducing differentiation. In one aspect, the base medium of the invention is serum-free and can be supplemented with differentiation-inducing factors and agents to induce and support differentiation of adipose tissue-derived stem cells. In one aspect, the medium is useful for inducing differentiation of adipose tissue-derived stem cells along differentiation pathways selected from the group consisting of adipose, chondrogenic, and osteogenic. One of ordinary skill in the art would appreciate that the base medium of the invention can be supplemented with various growth factors, hormones, and other agents useful in inducing and maintaining differentiation of various cell types, including, adipogenic, chondrogenic, and osteogenic. It is also known that ASCs can be induced to differentiate along neural and myogenic lineages (cardiac, skeletal, and smooth muscle). It is anticipated that the base medium of the invention will be useful for inducing differentiation of such cell types when supplemented with the appropriate differentiation-inducing agents.

The present invention provides a chemically-defined growth and differentiation medium useful for tissue engineering and basic science research to study, inter alia, the influence of specific chemicals, drugs, and growth factors on cells of the invention. The lack of serum in the medium further provides for less interference when specific antibodies or staining techniques are being utilized. In one embodiment, the lack of serum in the medium also allows for simpler purification and identification steps necessary to identify growth factors or other biological compounds secreted into the medium.

Briefly, the basic components can comprise: a basal medium such as DMEM/F12, antibiotics, antimycotics, nutrients (amino acids, fatty acids, minerals), growth factors, and/or hormones. In one aspect, the ingredients comprise a supplemented defined medium including DMEM/F12, L-glutamine, an antibiotic, an antimycotic, ITS+3 (such as Sigma I-2771; an insulin, transferrin, and selenium composition), a fatty acid supplement, non-essential amino acids, ascorbic acid 2-phosphate (ASAP), PDGF-BB, EGF, SCGF-$\beta$, TNF$\alpha$, IL-1$\beta$, beta-estradiol, progesterone, dexamethasone, and hydrocortisone. In one aspect, the protein and hormone supplements are human. One of ordinary skill in the art will appreciate that media other than DMEM F12 could be modified for use as well. In another aspect, serum can be added. In one aspect, the serum is used at low concentrations. In one aspect, the serum is used at concentrations as low as about 0.5%. In one aspect, the serum is human serum.

In one embodiment, cells of the invention are plated onto culture dishes which have been coated with at least one adhesion factor. In one aspect, other coatings are applied to the tissue culture dish. In one aspect, adhesion factors are added to the medium.

Various aspects and embodiments of the invention are described in further detail below.

BRIEF DESCRIPTION OF THE DRAWINGS

FIG. 2, comprising

FIG. 3, comprising panels 3A-3F, represents images of photomicrographs depicting multilineage differentiation potential (adipocyte-left photos: A and D; osteocyte-center photos: B and E; chondrocyte-right photos: C and F. of passage 3 ASCs cultured in serum-free AR8 (upper photos) and 0.5% human serum AR8 (lower photos). (scale bar=50 μm).

DETAILED DESCRIPTION OF THE INVENTION

Abbreviations and Acronyms

Figures 1A, 1B:
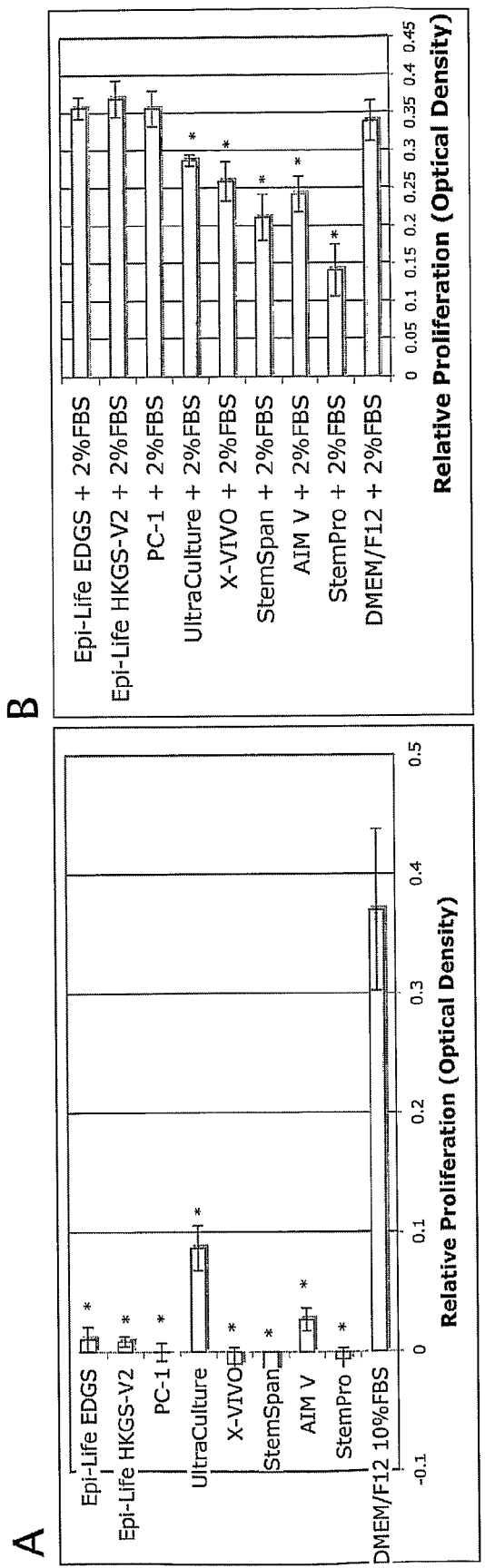
FIG. 1 is a graphic representation of MTS proliferation assay results examining: A) eight proprietary serum-free media in comparison to standard ASC cultured in DMEM/F12+10% FBS; and B) each base medium when supplemented with 2% FBS. *p<0.05.
Figures 2A, 2B, 2C:
FIGS. 2A-2C, represents images of photomicrographs which demonstrate the representative morphology of ASCs culture in AR8 medium containing 0.5% human serum (left panel; A), serum-free AR8 (center panel; B), and in DMEM/F12 containing 10% FBS (right panel; C). The scale indicates 100 μm.

ABAM—antibiotic antimycotic
AR8sf—serum-free AR8 medium
ASAP—ascorbic acid 2-phosphate
ASC—adipose-derived stromal or stem cell
BSA—bovine serum albumin
CPC—cetylpyridinium chloride
D10% FBS—DMEM/F12+10% FBS+1% ABAM
DMEM—Dulbecco's modified Eagle's medium
EGF—epidermal growth factor
FBS—fetal bovine serum
hASC—human adipose-derived stromal cell
HS—human serum (also referred to as HmS herein)
HSA—human serum albumin
IL-1β—interleukin-1 beta
ITS—insulin, transferrin, selenium
NEAA—non-essential amino acids
P—passage
PBS—phosphate buffered saline
PDGF—platelet-derived growth factor
PLA—processed lipoaspirate cells
SCGF-β—stem cell growth factor-β
SFM—serum-free medium (also referred to as sf herein)
TNFα—tumor necrosis factor alpha

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "additional supplements" as used in the context of a growth or differentiation medium refers to any compounds or agents being added to the medium, including, but not limited to, growth factors, hormones, vitamins, amino acids, attachment factors, matrix proteins, and other useful supplements. One of ordinary skill in the art will realize that the specific supplement and its amount may vary, and the specific supplement and its amount can be determined by techniques described herein and by those known in the art.

Adipose-derived stem cells or "adipose-derived stromal cells" refer to cells that originate from adipose tissue.

By "adipose" is meant any fat tissue. The terms "adipose" and "adipose tissue" are used interchangeably herein. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, most preferably, the adipose tissue is human. A convenient source of adipose tissue is from liposuction surgery, however, the source of adipose tissue or the method of isolation of adipose tissue is not critical to the invention.

The term "adult" as used herein, is meant to refer to any non-embryonic or non-juvenile animal. For example the term "adult adipose tissue stem cell," refers to an adipose stem cell, other than that obtained from an embryo or juvenile animal.

As used herein, the term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |

| Full Name | Three-Letter Code | One-Letter Code |
|---|---|---|
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

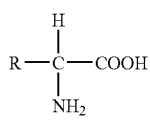

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "basal medium", as used herein, refers to a minimum essential type of medium, such as Dulbecco's Modified Eagle's Medium, Ham's F12, Eagle's Medium, RPMI, etc., to which other ingredients may be added. The term does not exclude media which have been prepared or are intended for specific uses, but which upon modification can be used for other cell types, etc.

The term "biocompatible," as used herein, refers to a material that does not elicit a substantial detrimental response in the host.

The terms "cell" and "cell line," as used herein, may be used interchangeably. All of these terms also include their progeny, which are any and all subsequent generations. It is understood that all progeny may not be identical due to deliberate or inadvertent mutations.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

A "compound," as used herein, refers to any type of substance or agent that is commonly considered a drug, or a candidate for use as a drug, combinations, and mixtures of the above, as well as polypeptides and antibodies of the invention.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The term "delivery vehicle" refers to any kind of device or material which can be used to deliver cells in vivo or can be added to a composition comprising cells administered to an animal. This includes, but is not limited to, implantable devices, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. As used herein, an "effective amount" means an amount sufficient to produce a selected effect. The term "effective amount" is used interchangeably with "effective concentration" herein.

The term "feeder cells" as used herein refers to cells of one type that are co-cultured with cells of a second type, to provide an environment in which the cells of the second type can be maintained, and perhaps proliferate. The feeder cells can be from a different species than the cells they are supporting. The terms, "feeder cells", "feeders," and "feeder layers" are used interchangeably herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" molecule is a molecule in a form in which it exhibits a property or activity by which it is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See the NCBI website.

The percent identity between two sequences can be determined using techniques similar to those described above, with or without allowing gaps. In calculating percent identity, typically exact matches are counted. The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, means to suppress or block, an activity or function such that it is lower relative to a control value. The inhibition can be via direct or indirect mechanisms. In one aspect, the activity is suppressed or blocked by at least 10% compared to a control value, more preferably by at least 25%, and even more preferably by at least 50%.

The term "inhibitor" as used herein, refers to any compound or agent, the application of which results in the inhibition of a process or function of interest, including, but not limited to, differentiation and activity. Inhibition can be inferred if there is a reduction in the activity or function of interest.

The term "injury" refers to any physical damage to the body caused by violence, accident, trauma, or fracture, etc.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

Used interchangeably herein are the terms "isolate" and "select".

The term "isolated," when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays which distinguish cell types.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, *Antibodies, A Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "modulate", as used herein, refers to changing the level of an activity, function, or process. The term "modulate" encompasses both inhibiting and stimulating an activity, function, or process.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Plurality" means at least two.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified", relates to an enrichment of a cell, cell type, molecule, or compound relative to other components normally associated with the cell, cell type, molecule, or compound in a native environment. The term "purified" does not necessarily indicate that complete purity of the particular cell, cell type, molecule, or compound has been achieved during the process. A "highly purified" cell or compound as used herein refers to a cell or compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In one aspect, the activity or differentiation is stimulated by at least 10% compared to a control value, more preferably by at least 25%, and even more preferably by at least 50%. The term "stimulator" as used herein, refers to any compound or agent, the application of which results in the stimulation of a process or function of interest, including, but not limited to, ASC cell production, differentiation, and activity, as well as that of ASC progeny.

A "subject" of analysis, diagnosis, or treatment is an animal. Such animals include mammals, preferably a human.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The use of the phrase "tissue culture dish or plate" refers to any type of vessel which can be used to plate cells for growth or differentiation.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear or rupture to a tissue or cell layer. A wound may occur by any physical insult, including a surgical procedure.

The present invention lies in the significant discovery that adipose tissue cells can be isolated and grown in serum-free medium. The present invention provides methods and compositions for the culture of adipose tissue-derived cells and their differentiation into various cell types.

The cells produced by the methods of invention are useful in providing a source of adipose tissue-derived cells with the ability to differentiate into various cell types, including, but no limited to, adipocytes, chondrocytes, and osteoblasts, as well as provide fully differentiated and functional cells for research, transplantation, and development of tissue engineering products for the treatment of diseases and disorders and traumatic injury repair. Thus, in one aspect, the invention provides a method for differentiating adipose tissue-derived cells along several pathways or lineages and into functional cell types.

In one embodiment of the invention, enriched populations can be used for tissue engineering applications in which bone needs to be remodeled or removed, or drugs need to be delivered to a tissue, such as bone. The invention encompasses various methods for enriching populations of adipose tissue-derived cells from adipose tissue and propagating the cells in culture. The present invention further provides compositions and methods for growing adipose tissue-derived cells in serum-free medium and for inducing differentiation of adipose-tissue derived stem cells in serum-free medium.

The adipose tissue-derived cells useful in the methods of invention can be isolated by a variety of methods known to those skilled in the art such as described in WO 00/53795. In a preferred method, adipose tissue is isolated from a mammalian subject, preferably a human subject. A preferred source of adipose is subcutaneous adipose tissue. Another preferred source of adipose tissue is omental adipose. In humans, the adipose is typically isolated by liposuction. If the cells of the invention are to be transplanted into a human subject, it is preferable that the adipose tissue be isolated from that same subject to provide for an autologous transplant. Alternatively, the transplanted cells are allogeneic.

Adipose tissue-derived cells represent a stem cell source that can be harvested routinely with minimal risk or discomfort to the subject. They can be expanded ex vivo, differentiated along unique lineage pathways, genetically engineered, and re-introduced into individuals as either autologous or allogeneic transplantation.

The present invention provides methods and compositions for growing adipose stem cells. In one embodiment, serum-free culture medium is provided. In another embodiment, the invention provides culture medium and techniques for enhancing proliferation of adipose tissue cells. In one aspect, the invention provides methods and compositions for enhancing proliferative rates of adipose stem cells and their progeny, which include precursors for various cell types. In one aspect, the methods of enriching such cells includes methods of inducing proliferation and of inducing differentiation of the precursor cells.

The present invention provides methods for identifying and characterizing populations of adipose stem cells and derivatives and progeny thereof.

In general, cell culture media provide the nutrients necessary to maintain and grow cells in a controlled, artificial, and in vitro environment. Characteristics and compositions of cell culture media vary depending on the particular cellular requirements. Important parameters include osmolarity, pH, and nutrient formulations.

Typically, cell culture medium formulations are supplemented with a range of additives, including undefined components such as fetal bovine serum (FBS) (5-20% v/v) or extracts from animal embryos, organs or glands (0.5-10% v/v). While FBS is the most commonly applied supplement in animal cell culture media, other serum sources are also routinely used, including newborn calf, horse, and human. Organs or glands that have been used to prepare extracts for the supplementation of culture media include submaxillary gland (Cohen (1961) J. Biol. Chem. 237: 1555-1565), pituitary (Peehl and Ham (1980) In Vitro 16: 516-525; see U.S. Pat. No. 4,673,649), hypothalamus (Maciag, et al. (1979) Proc. Natl. Acad. Sci. USA 76: 5674-5678; Gilchrest, et al. (1984) J. Cell. Physiol. 120: 377-383), and brain (Maciag, et al. (1981) Science 211: 1452-1454). These types of chemically undefined supplements serve several useful functions in cell culture media (see Lambert, et al. (1985) In: Animal Cell Biotechnology, Vol. 1, Spier et al., Eds., Academic Press, New York, pp. 85-122 (1985)). For example, these supplements (1) provide carriers or chelators for labile or water-insoluble nutrients; (2) bind and neutralize toxic moieties; (3) provide hormones and growth factors, protease inhibitors and essential, often unidentified or undefined low molecular weight nutrients; and (4) protect cells from physical stress and damage. Thus, serum or organ/gland extracts are commonly used as relatively low-cost supplements to provide an optimal culture medium for the cultivation of animal cells. "Non-peptide growth factors" refers to non-peptide compounds such as steroids, retinoids and other chemical compounds or agents which regulate cell growth and differentiation. It is generally recognized that concentrations may vary.

The present invention provides serum-free culture conditions for growing adipose tissue-derived cells and for inducing differentiation of such cells along different pathways. In one aspect, the invention provides pretreating the tissue culture dishes with factors which enhance cell adhesion and attachment.

A number of so-called "defined" media, which avoid the use of animal serum (and/or animal extracts), have also been developed. These media, which often are specifically formulated to support the culture of a single cell type, contain no undefined supplements and instead incorporate defined quantities of purified growth factors, proteins, lipoproteins and other substances usually provided by the serum or extract supplement. Because the components (and concentrations thereof) in such culture media are precisely known, these media are generally referred to as "defined culture media." Often used interchangeably with "defined culture medium" is the term "serum-free medium" or "SFM." A number of SFM formulations are commercially available, such as those designed to support the culture of endothelial cells, keratinocytes, melanocytes, mammary epithelial cells, monocytes/macrophages, fibroblasts, chondrocytes, and hepatocytes. The distinction between SFM and defined media, however, is that SFM are media devoid of serum, but not necessarily of other undefined components such as organ/gland extracts.

Some extremely simple defined media, which consist essentially of vitamins, amino acids, organic and inorganic salts and buffers, have been used for cell culture. Such media (often called "basal media") are often deficient in the nutritional content required by most animal cells and may incorporate into the basal medium additional components to make the medium more nutritionally complex, but to maintain the serum-free and low protein content of the media. Non-limiting examples of such components include serum albumin from bovine (BSA) or human (HSA); certain growth factors derived from natural (animal) or recombinant sources; lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements (reviewed by Waymouth (1984) In: Cell Culture Methods for Molecular and Cell Biology, Vol. 1: Methods for Preparation of Media, Supplements, and Substrata for Serum-Free Animal Cell Culture, Barnes et al., eds., New York: Alan R. Liss, Inc., pp. 23-68; and by Gospodarowicz, Id., at pp 69-86).

The advantages of using serum-free media and defined media for drug screening and generation of cellular products for clinical use are well-known in the art. These advantages include, but are not limited to, absence of adventitious organisms such as animal retroviruses, greater control of batch-to-batch variability, and defined levels of known modulators of cell function and activity.

One of ordinary skill in the art will appreciate that culture conditions such as cell seeding densities can be selected for each experimental condition or intended use.

Many techniques are known to those of skill in the art for measuring adipose, chondrogenic, and osteogenic differentiation and those not described herein are encompassed within the techniques of the invention.

Cell culture models for various disorders are useful, e.g., for testing the ability of a compound to modulate a cellular process associated with the disorder. The adipose tissue-derived stem cells described herein are useful, e.g., for providing a pool of cells that can be differentiated at will and used in assays of such compounds.

Human adipose tissue-derived adult stromal cells represent an adult stem cell source that can be harvested routinely with minimal risk or discomfort to the patient. They can be expanded ex vivo, differentiated along unique lineage pathways, genetically engineered, and re-introduced into individuals as either autologous or allogeneic transplantation.

Methods for the isolation, expansion, and differentiation of human adipose tissue-derived cells have been reported. See for example, Burris et al. 1999, Mol Endocrinol 13:410-7; Erickson et al. 2002, Biochem Biophys Res Commun. Jan. 18, 2002; 290(2):763-9; Gronthos et al. 2001, Journal of Cellular Physiology, 189:54-63; Halvorsen et al. 2001, Metabolism 50:407-413; Halvorsen et al. 2001, Tissue Eng. 7(6):729-41; Harp et al. 2001, Biochem Biophys Res Commun 281:907-912; Saladin et al. 1999, Cell Growth & Diff 10:43-48; Sen et al. 2001, Journal of Cellular Biochemistry 81:312-319; Zhou et al. 1999, Biotechnol. Techniques 13:513-517. Adipose tissue-derived stromal cells are obtained from minced human adipose tissue by collagenase digestion and differential centrifugation [Halvorsen et al. 2001, Metabolism 50:407-413; Hauner et al. 1989, J Clin Invest 84:1663-1670; Rodbell et al. 1966, J Biol Chem 241:130-139].

Adult human extramedullary adipose tissue-derived stromal cells represent a stromal stem cell source that can be harvested routinely with minimal risk or discomfort to the patient. Pathologic evidence suggests that adipose-derived stromal cells are capable of differentiation along multiple lineage pathways. Adipose tissue is readily accessible and abundant in many individuals. Obesity is a condition of epidemic proportions in the United States, where over 50% of adults exceed the recommended BMI based on their height.

It is well documented that adipocytes are a replenishable cell population. Even after surgical removal by liposuction or other procedures, it is common to see a recurrence of adipocytes in an individual over time. This suggests that adipose tissue contains stromal stem cells and/or precursors that are capable of self-renewal.

Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there are up to $8.6 \times 10^4$ stromal cells per gram of adipose tissue (Sen et al., 2001, J. Cell. Biochem., 81:312-319). Ex vivo expansion over 2 to 4 weeks yields up to 500 million stromal cells from 0.5 kilograms of adipose tissue. These cells can be used immediately or cryopreserved for future autologous or allogeneic applications.

Adipose derived stromal cells also express a number of adhesion and surface proteins. These include cell surface markers such as CD9; CD29 (integrin beta 1); CD44 (hyaluronate receptor); CD49d,e (integrin alpha 4, 5); CD54 (ICAM1); CD55 (decay accelerating factor); CD105 (endoglin); CD106 (VCAM-1); CD166 (ALCAM) and HLA-ABC (Class I histocompatibility antigen); and cytokines such as interleukins 6, 7, 8, 11; macrophage-colony stimulating factor; GM-colony stimulating factor; granulocyte-colony stimulating factor; leukemia inhibitory factor; stem cell factor and bone morphogenetic protein. Many of these proteins have the potential to serve a hematopoietic supportive function and all of them are shared in common by bone marrow stromal cells.

The adipose tissue derived stromal cells useful in the methods of invention can be isolated by a variety of methods known to those skilled in the art, such as described in WO 00/5379. In a preferred method, adipose tissue is isolated from a mammalian subject, preferably a human subject. In humans, the adipose is typically isolated by liposuction. If the cells of the invention are to be transplanted into a human subject, it is preferable that the adipose tissue be isolated from that same subject to provide for an autologous transplant. Alternatively, the transplanted cells are allogeneic.

Cells described herein can be isolated from adipose tissue using methods previously described (Zuk et al., Tissue Engineering 7:211, 2001; Katz et al., Stem Cells 23:412, 2005). However, one of ordinary skill in the art will appreciate that culture conditions such as cell seeding densities can be selected for each experimental condition or intended use. Other techniques useful for isolating and characterizing the cells described herein include fractionating cells using cell markers.

US 2002/0076400 and WO 00/53795 describe the production of multipotent cell populations from human adipose tissue. Said cell populations can be differentiated into adipocytes, osteoblasts, chondrocytes, and myocytes. The publications indicate that some of the cells they can be maintained in culture in vitro for at least 15 cell transfers without losing their multipotent character.

U.S. Pat. No. 6,800,480 describes methods and materials for growing primate-derived primordial stem cells in a feeder cell-free culture system.

Many techniques are known to those of ordinary skill in the art for measuring adipocyte differentiation, as well as the differentiation of other mesenchymal cells and those not described herein are encompassed within the techniques of the invention.

Cell culture models for various disorders are useful, e.g., for testing the ability of a compound to modulate a cellular process associated with the disorder. The adipose tissue-derived stromal cells described herein are useful, e.g., for providing a pool of cells that can be differentiated at will and used in assays of such compounds.

The invention further provides for methods of using such cells in toxicological, carcinogen, and drug screening methods, as well as in therapeutic applications where tissue or cell growth, stability, and function is enhanced or otherwise supplanted using such cells.

In one embodiment, adipose tissue, or cells derived from adipose tissue, are subjected to varied culture media conditions as described herein to support growth or differentiation under serum-free or low serum conditions. One of ordinary skill in the art will appreciate that the amount of each growth factor, hormone, compound, nutrient, vitamin, etc., used may vary according to the culture conditions, amount of additional differentiation-inducing agent used, or the number of combination of agents used when more than one agent is used.

Some examples of diseases, disorder, conditions, and injuries that may be treated according to the methods of the invention are discussed herein. The invention should not be construed as being limited solely to these examples, as other diseases that are at present unknown, once known, may also be treatable using the methods of the invention.

The present invention also encompasses pharmaceutical and therapeutic compositions comprising the adipose tissue-derived stem cells, purified cells derived therefrom, or progeny of such cells. In one embodiment of the invention, therapies are provided for diseases, disorders, conditions, and injuries associated with aberrant cell function, activity, numbers, or regulation. Because of the ease of isolation of ASCs and abundance of adipose tissue, these methods are superior to others using bone marrow aspirates, stem cells or circulating blood cells to produce cells. In one aspect, the invention provides administering to a subject in need thereof a pharmaceutical composition comprising a therapeutically effective amount of adipose tissue-derived stem cells, precursors, and progeny.

The present invention provides methods for administering ASCs and their progeny to subjects in need thereof. In one aspect, the ASCs have been pretreated to differentiate into a precursor cell of interest or into a fully differentiated state. In another aspect, populations of ASCs can be treated with more than one type of differentiation inducing agent or medium, or a combination of agents, which induce more than one type of differentiation. In another aspect, separate populations of ASCs, that have been pretreated with cell differentiation-inducing compounds, or no treatment at all, can be co-administered to a subject. Co-administration of different groups of cells does not necessarily mean that the ASC populations are actually administered at the same time or that the populations are combined or administered in the same composition. The invention further provides compositions and methods for administering ASCs to subjects and then inducing the ASCs to differentiate in vivo by also administering cell differentiation-inducing agents to the subject. In one aspect, the subject is a human. When more than one differentiation agent or compound is used to induce cells along a particular cell pathway, or when additional agents are also used to induce some of the cells to differentiate along a second pathway, the various agents need not be provided at the same time. Various compounds and growth factors can be used with the cells of the invention to induce or modulate differentiation or maturation.

The cells of the present invention may be administered to a subject alone or in admixture with a composition useful in the repair of tissue, bone, and vascular injury and defects. Such compositions include, but are not limited to bone morphogenetic proteins, hydroxyapatite/tricalcium phosphate particles (HA/TCP), gelatin, poly-L-lysine, and collagen.

Non-synthetic matrix proteins like collagen, glycosaminoglycans, and hyaluronic acid, which are enzymatically digested in the body, are useful for delivery to bone areas (see U.S. Pat. Nos. 4,394,320; 4,472,840; 5,366,509; 5,606,019; 5,645,591; and 5,683,459) and are suitable for use with the present invention. Other implantable media and devices can be used for delivery of the cells of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The cells of the present invention can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

In one embodiment, a composition comprising the cells of the invention is administered locally by injection. Compositions comprising the cells can be further combined with known drugs, and in one embodiment, the drugs are bound to the cells. These compositions can be prepared in the form of an implantable device that can be molded to a desired shape. In one embodiment, a graft construct is prepared comprising a biocompatible matrix and one or more cells of the present invention, wherein the matrix is formed in a shape to fill a gap or space created by the removal of a tumor, injured, or diseased tissue.

The cells can be seeded onto the desired site within the tissue to establish a population. Cells can be transferred to sites in vivo using devices such as catheters, trocars, cannulae, stents (which can be seeded with the cells), etc.

The present invention thus provides methods and compositions for delivering incredibly large numbers of ASCs, precursors, or differentiated cells derived from adipose tissue for the procedures and treatments described herein. Additionally, for diseases that require cell infusions or administration, adipose tissue harvest is minimally invasive, yields many cells, and can be done repeatedly The present invention encompasses the preparation and use of immortalized cell lines, including, but not limited to, adipose tissue-derived cell lines capable of differentiating into at least one cell type. Various techniques for preparing immortalized cell lines are known to those of ordinary skill in the art.

The present invention also encompasses the preparation and use of cell lines or cultures for testing or identifying agents for their effects on adipose tissue or bone. The present invention further encompasses compounds, which are identified using any of the methods described herein. Such compounds may be formulated and administered to a subject for treatment of the diseases, disorders, conditions, and injuries disclosed herein.

In one embodiment, genes of interest can be introduced into cells of the invention. In one aspect, such cells can be administered to a subject. In one aspect, the subject is afflicted with a disease, disorder, condition, or injury. In one aspect, the cells are modified to express exogenous genes or are modified to repress the expression of endogenous genes, and the invention provides a method of genetically modifying such cells and populations. In accordance with this method, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA (e.g., antisense RNA or a ribozyme). Thus, for example, the coding polynucleotide can encode a gene conferring resistance to a toxin, a hormone (such as peptide growth hormones, hormone releasing factors, sex hormones, adrenocorticotrophic hormones, cytokines (e.g., interferons, interleukins, lymphokines), a cell-surface-bound intracellular signaling moiety (e.g., cell adhesion molecules, hormone receptors), a factor promoting a given lineage of differentiation, etc.

In addition to serving as useful targets for genetic modification, many cells and populations of the present invention secrete various polypeptides. Such cells can be employed as bioreactors to provide a ready source of a given hormone, and the invention pertains to a method of obtaining polypeptides from such cells. In accordance with the method, the cells are cultured under suitable conditions for them to secrete the polypeptide into the culture medium. After a suitable period of time, and preferably periodically, the medium is harvested and processed to isolate the polypeptide from the medium. Any standard method (e.g., gel or affinity chromatography, dialysis, lyophilization, etc.) can be used to purify the hormone from the medium, many of which are known in the art.

In other embodiments, cells (and populations) of the present invention secreting polypeptides can be employed as therapeutic agents. Generally, such methods involve transferring the cells to desired tissue, either in vitro or in vivo, to animal tissue directly. The cells can be transferred to the desired tissue by any method appropriate, which generally will vary according to the tissue type.

Compositions comprising cells of the invention can be employed in any suitable manner to facilitate the growth and differentiation of the desired tissue. For example, the composition can be constructed using three-dimensional or stereotactic modeling techniques. To direct the growth and differentiation of the desired structure, the composition can be cultured ex vivo in a bioreactor or incubator, as appropriate. In other embodiments, the structure is implanted within the host animal directly at the site in which it is desired to grow the tissue or structure. In still another embodiment, the composition can be engrafted onto a host, where it will grow and mature until ready for use. Thereafter, the mature structure (or anlage) is excised from the host and implanted into the host, as appropriate.

Matrices suitable for inclusion into the composition can be derived from various sources. As discussed above, the cells, matrices, and compositions of the invention can be used in tissue engineering and regeneration. Thus, the invention pertains to an implantable structure (i.e., an implant) incorporating any of these inventive features. The exact nature of the implant will vary according to the intended use. The implant can be, or comprise, as described, mature or immature tissue. Thus, for example, one type of implant can be a bone implant, comprising a population of the inventive cells that are undergoing (or are primed for) adipose, chondrogenic, or osteoclastic differentiation, optionally seeded within a matrix material. Such an implant can be applied or engrafted to encourage the generation or regeneration of mature bone or other tissue within the subject.

One of ordinary skill in the art would appreciate that there are other carriers useful for delivering the cells of the invention. Such carriers include, but are not limited to, calcium phosphate, hydroxyapatite, and synthetic or natural polymers such as collagen or collagen fragments in soluble or aggregated forms. In one aspect, such carriers serve to deliver the cells to a location or to several locations. In another aspect, the carriers and cells can be delivered either through systemic administration or by implantation. Implantation can be into one site or into several sites.

In certain useful applications, compounds are screened specifically for potential toxicity. Cytotoxicity can be determined in the first instance by the effect on cell viability, survival, morphology, and leakage of enzymes into the culture medium. Other methods to evaluate toxicity include determination of the synthesis and secretion of target proteins of interest and induction of apoptosis (indicated by cell rounding, condensation of chromatin, and nuclear fragmentation). DNA synthesis can be measured using assays such as tritiated-thymidine or BrdU incorporation. Effects of a drug on DNA synthesis or structure can be determined by measuring DNA synthesis or repair. Aberrant DNA synthesis, especially at unscheduled times in the cell cycle, or above the level required for cell replication, is consistent with a drug effect. Unwanted effects can also include unusual rates of sister chromatid exchange, determined by metaphase spread (see pp 375-410 of Vickers (1997) In vitro Methods in Pharmaceutical Research Academic Press).

In one embodiment, the cells of the invention are used to screen factors that promote cell differentiation or promote proliferation and maintenance of such cells, or precursors, in long-term culture. Assays are known in the art for measuring cell differentiation of cells known to be derived from adipose tissue, as well as for proliferation. Such factors can be known drugs, agents, proteins, nucleic acids, etc., which can be used to treat cells using the assays and methods described herein or which are known in the art.

In another embodiment, cells of the invention are used to screen factors that inhibit cell differentiation.

In yet another embodiment, differentiated or undifferentiated cells of the invention are used to screen factors that modulate production, differentiation, function, and activity of a cell of interest derived from the adipose tissue derived stem cells as cultured herein.

In general, methods for the identification of a compound which effects the differentiation, production, activity, or function of a cell of the invention, include the following general steps:

The test compound is administered to a cell, tissue, sample, or subject, in which the measurements are to be taken. A control is a cell, tissue, sample, or subject in which the test compound has not been added. A higher or lower level of the indicator or parameter being tested, i.e., cell number, differentiation, activity, function, etc., in the presence of the test compound, compared with the levels of the indicator or parameter in the sample which was not treated with the test compound, is an indication that the test compound has an effect on the indicator or parameter being measured, and as such, is a candidate for modulation of the desired activity. Test compounds may be added at varying doses and frequencies to determine the effective amount of the compound which should be used and effective intervals in which it should be administered. In another aspect, a derivative or modification of the test compound may be used.

In one embodiment, antibodies can be used to identify stem or precursor cells or cell markers. In another embodiment, antibodies directed against proteins of cells of the invention can be used to modulate the activity of the proteins. The invention encompasses preparing such antibodies.

Antibodies may be generated using methods that are well known in the art. For instance, U.S. patent application Ser. No. 07/481,491, which is incorporated by reference herein in its entirety, discloses methods of raising antibodies to specific proteins. For the production of antibodies, various host animals, including but not limited to rabbits, mice, and rats, can be immunized by injection with a specific polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum.*

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and*

Cancer Therapy, Alan R. Liss, Inc., pp. 77-96) may be employed to produce human monoclonal antibodies. In another embodiment, monoclonal antibodies are produced in germ-free animals utilizing the technology described in international application no. PCT/US90/02545, which is incorporated by reference herein in its entirety.

In accordance with the invention, human antibodies may be used and obtained by utilizing human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain ($CH_1$) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The invention also includes a kit comprising cells of the invention, compositions of the invention, compounds of the invention, and an instructional material which describes administering or using the cells, compositions, and compounds. In another embodiment, this kit comprises a (preferably sterile) solvent suitable for dissolving or suspending the composition of the invention prior to administering the composition.

As used herein, an "instructional material" includes a publication, a recording, a diagram, or any other medium of expression which can be used to communicate the usefulness of the invention in the kit for effecting enrichment and growth of adipose stem cells. Optionally, or alternately, the instructional material may describe one or more methods of alleviation the diseases or disorders in a cell or a tissue of a mammal. The instructional material of the kit of the invention may, for example, be affixed to a container which contains the compositions of the invention or be shipped together with a container which contains the antibody. Alternatively, the instructional material may be shipped separately from the container with the intention that the instructional material and the compound be used cooperatively by the recipient.

EXAMPLES

Example 1

General Methods

Human adipose tissue-derived adult stromal cells represent a stem cell source that can be harvested routinely with minimal risk or discomfort to the patient. They can be expanded ex vivo, differentiated along unique lineage pathways, genetically engineered, and re-introduced into individuals via either autologous or allogeneic transplantation.

Methods described herein, or which are known in the art, can be used to isolate adipose tissue and adipose stem cells, which in turn can be subjected to the defined medium of the invention.

Kim et al. demonstrated the feasibility of 10% human serum supplementation to support proliferation and subsequent differentiation of adipose stem cells [14]. Further reduction in this serum requirement could greatly improve the translatable utility of this approach. In an effort to address these challenges, the present application discloses two new media formulations. The first, a completely serum-free formulation, supports human ASC growth in culture for 3-4 weeks. The second includes 0.5% human serum, an amount obtainable through a small autologous blood draw. This low serum medium supports rapid ASC growth for up to 4 months in culture. Cells grown in both media maintain their multipotentiality and the expression of several markers of putative stem cells.

Materials and Methods

Adipose Stem Cell Isolation

Subcutaneous adipose tissue was obtained from patients undergoing elective surgical procedures in the Department of Plastic Surgery, University of Virginia in accordance with the University's Human Investigation Committee. Discarded panniculectomy specimens and liposuction aspirates from 10 female patients (median age=40, range 30-58 years old) were processed as described previously [15,16]. Briefly, the specimens were mechanically liposuctioned as necessary under sterile conditions and washed with Hanks solution with Ca++ and Mg++.

The aspirate was then digested in Liberase Blendzyme 1 (Roche 1 988 417, 9 mg/ml) for 30-60 minutes until reaching a smooth and even consistency. A cellular pellet was isolated via centrifugation, filtered through 250 µm nylon mesh, washed with erythrocyte lysis buffer, refiltered at 105 µm, and resuspended in serum-free DMEM/F12+1% Antibiotic Antimycotic (Gibco 15420-062).

For proliferation, differentiation, and flow characterization studies, the pellet was divided and plated into two formulations, DMEM/F12+10% FBS+1% ABAM (D10% FBS), and the newly developed low serum medium described herein. Following the first passage, cells grown in low serum were divided into serum-free and low serum groups. Cells isolated for use in media development and serum lot screening were initially plated in D10% FBS, and subsequently switched to their respective test media.

The cell lines obtained and tested include: 41229, 41115L, 50209L, 50209 (2 samples from same patient), 50225L, 50401L, 50422L, 50503, 5-01, 5-02, and 5-05.

Proprietary Serum-Free Medium Testing

Initial efforts were made to identify a suitable serum-free medium for use with ASCs. Eight commercially available proprietary media were screened for their ability to support ASC growth in culture (StemPro-34 (Gibco 10639+ nutrient supplement 10641), AIM V (Gibco 87-0112), StemSpan (StemCell Technologies 09600), X-VIVO 15 (Cambrex 04-418Q), UltraCulture (Cambrex 12-725F), PC-1 (Cambrex 77232), Epi-Life HKGS-V2 (Cascade medium M-EPI-500-CA+Human Keratinocyte Growth Supplement V2 S-014-5), and Epi-Life EDGS (Cascade medium M-EPI-500-CA+EpiLife Defined Growth Supplement S-012-5)). Initial subjective attachment observations identified three of the eight media (StemPro, AIM V, and StemSpan) as requiring prior coating of culture plastic with 10% HS to allow attachment. Cells cultured in uncoated plates attached without difficulty in the other five formulations tested. Following coating as necessary, early passage cells were plated at $2 \times 10^3$ cells/cm$^2$ in 96 well dishes, cultured in each test medium, as well as the standard medium DMEM/F12+10% FBS, and assayed for cell proliferation using the MTS Promega One Solution Proliferation Assay per manufacturers instructions. Results were read on an absorbance colorimetric plate reader at 490 nm.

Media Development

Early passage cells were plated at $2 \times 10^3$/cm$^2$ in 96 well plates in an initial base medium consisting of DMEM/F12 (Gibco Cat. No. 11320-033 Invitrogen Corp), L-glutamine (Gibco Cat. No. 25030-081 Invitrogen Corp), dexamethasone (Sigma D8893), ascorbic acid 2-phosphate (Sigma A-8960), ITS+3 (Sigma 1-2771), fatty acid supplement (Sigma F-7050), non-essential amino acids (Gibco Cat. No. 11140-050 Invitrogen Corp.), and antibiotic-antimycotic (Gibco Cat. No. 15240-062 Invitrogen Corp.). Additional supplements were individually screened for their effect on cell proliferation using an MTS assay (Promega One Solution Proliferation Assay). Those supplements that increased proliferation above the base recipe were added to the base, and the remaining supplements were screened again. 0.5% human serum (Cambrex 14-402E; lot#01104654) was added to the base media during testing in order to support a basal growth rate while additional factors were screened. The final formulation was then tested both with and without this added serum.

Initial supplements tested included L-glutamine (Gibco 25030-081), Antibiotic Antimycotic (Gibco 15240-062), ITS+3 liquid media supplement (Sigma 1-2771), ITS liquid media supplement (Sigma 13146), fatty acid supplement (Sigma F-7050), MEM non-essential amino acids (Gibco 11140-050), and ASAP (Sigma A-8960), as well as 13 growth factors: PDGF-BB (Research Diagnostics Inc RDI-114b), SCGF-β (RDI-1022B), TNFα (RDI-301), IL-1 (RDI-201B), Flt-3 ligand (RDI-3019), HGF (RDI-1039), IGF-1 (RDI-11), SCF (RDI-307), SDF-1alpha (RDI-3028), VEGF (RDI-1029), TGFβ (RDI-1021R), EGF (R & D Systems 236EG), and bFGF (Sigma F 0291); 12 peptones: HyPep 4601 protein hydrolysate (Sigma H 6784), and Organotechnie plant peptone E1 (PPA), plant peptone ET1 (PPB), wheat peptone E1 (WPA), soy peptone A3SC(SPA), soy peptone A2SC (SPB), yeast extract (YE), ultrafiltrated yeast extract (UFYE), malt extract R2 (MER2), malt extract R3 (MER3), caseine peptone N1 (CPN1), and gelatin peptone N3 (GPN3); and 4 hormones: beta-estradiol (Sigma E2758-1G), progesterone (Sigma P8783-5G), dexamethasone (Sigma D-8893), and hydrocortisone (Sigma H0888-1G). Further pilot testing of a serum-free version of AR8 included the screening of attachment factors and varied plating densities. Collagen type I and IV, fibronectin, laminin, poly-D-lysine, and uncoated surfaces (BD Biosciences Multiwell Variety Pack 354431) were tested, as were plating densities of 2, 5, 7.5, 10, 15, and $20 \times 10^3$ cells/cm$^2$. Cell attachment and survival were assessed by direct microscopic observation.

Cell Culture

Human ASCs were cultured at 37° C., 5% $CO^2$ in each of three final media: D10% FBS; low serum media (AR80.5% human serum); and serum-free media (AR8 sf). The AR8 base is a highly supplemented defined medium including DMEM/F12 (Gibco Cat No. 11320-033), L-glutamine (Gibco Cat No. 25030-081), Antibiotic Antimycotic (ABAM, Gibco Cat No. 15240-062), ITS+3 (Sigma 1-2771), Fatty Acid Supplement (Sigma F-7050), MEM non-essential amino acids (Gibco Cat No. 11140-050), ascorbic acid 2-phosphate (Sigma A-8960), PDGF-BB (Research Diagnostics Inc RDI-114b), EGF (R & D Systems 236EG), SCGF-β (Research Diagnostics Inc RDI-1022B), TNFα (Research Diagnostics Inc RDI-301), IL-10 (Research Diagnostics Inc RDI-201B), beta-estradiol (Sigma E2758-1G), progesterone (Sigma P8783-5G), dexamethasone (Sigma D-8893), and hydrocortisone (Sigma H0888-1G). Cells were passed at confluence using the fungal derived enzyme TrypLE (Gibco Cat No. 12604-013) and counted on a hemocytometer using trypan blue exclusion. Cells were replated at $2 \times 10^{-3}$ cells/cm$^2$ for cells in the first two formulations, and at $1.5 \times 10^4$ cells/cm$^2$ for cells in the serum-free formulation. At the initial passage of cells plated into AR80.5% human serum (HS), half of the cells were switched to serum-free AR8 and half were maintained in their original formulation.

Adipogenic Differentiation

Passage 3 cells were plated into 12 well plates and allowed to reach confluency in their respective growth media. At confluence, wells were switched to adipogenic medium [DMEM/F12, 0.5 mM isobutyl-methylxanthine, 1 µM dexamethasone, 10 µM insulin, 200 µM indomethacin, 10% FBS, and 1% ABAM] or control medium [DMEM/F12, 10% FBS, and 1% ABAM]. Cells were maintained in culture for 2 weeks, fixed in 10% formalin for 10 minutes, and stained with Oil Red 0 (Sigma 00625). The percentage of cells containing lipid was calculated using 10 microscopic field of view counts at 20× magnification. The Oil red 0 in the lipid was then extracted with isopropanol, transferred to a 96 well plate, and read in a colorimetric absorbance plate reader at 490 nm as described in Ramirez-Zacarias et al. [17].

Osteogenic Differentiation

Passage 3 cells were cultured in parallel as described for adipogenesis. At confluence, cells were switched either to osteogenic medium [DMEM/F12, 0.1 μM dexamethasone, 50 μM ascorbate-2-phosphate, 10 mM beta-glycerophosphate, 1% ABAM, and 10% FBS] or control medium [DMEM/F12, 10% FBS, and 1% ABAM]. Cells were cultured for 2 weeks, fixed in ice-cold 70% ethanol, and stained with Alizarin Red S 1% aqueous solution-LabChem. A quantitative measure of bone matrix formation was preformed by solubilizing the alizarin stain for 15 minutes in 10% cetylpyridinium chloride (CPC), pH 7.0, and then reading the resultant solution on a colorimetric plate reader at 570 nm.

Chondrogenic Differentiation

Passage 3 cells were plated in micromass culture as 10 μl drops at $1 \times 10^5$ cells/drop as described in Huang et al. [18]. Briefly, cells were allowed to attach for 2 hours at which point they were gently covered with their respective growth media. At 24 hours, the medium was changed to either chondrogenic medium (DMEM/F12, 6.25 μg/ml insulin, 10 ng/ml TGFβ1, 50 nM ascorbate-2-phosphate, 1% ABAM, and 1% FBS), or non-differentiation control medium (DMEM/F12, 10% FBS, 1% ABAM). Cells were maintained in culture for 7 days, fixed in 4% paraformaldehyde, and stained with alcian blue (Sigma A 4045).

Flow Cytometry Characterization

Flow cytometry was performed using known techniques.

Serum Lot Screening

Passage 1 cells were plated uniformly at $2 \times 10^3$ cells/cm$^2$ in 96 well plates and allowed to attach overnight in DMEM/F12 containing 10% FBS. Medium was removed and the plates rinsed with serum-free DMEM/F12. Cells were fed investigational (test) media for an additional 7 days at which point a number of wells had reached approximately 80% confluence. Proliferation rates were analyzed with an MTS assay using the Promega CellTiter 96 Aqueous One Solution Cell Proliferation Assay per commercial instructions. Results were read on an absorbance colorimetric plate reader at 490 nm. Seven media compositions were tested with eight wells each including D10, AR8+0.5% FBS, and AR8+0.5% HS. Five lots of human serum, A-E, were screened. A and B-pooled Cambrex Human Serum lots 01104654 and 01109677; C-E-Innovative Research Inc Single Donor Human Serum lots GT052035, BT127172, and TT069329. Gibco Fetal Bovine Serum, Qualified lot 1228496.

Statistical Analysis

Comparisons between groups were analyzed using a 2-sided student T test. Probability values less than 0.05 were considered statistically significant.

Results

Commercially Available Serum-Free Media Testing

Eight commercially available serum-free media developed for use with other cell lines were screened for their ability to support human ASC growth in culture. None of the available media was sufficient for supporting cell growth as purchased, and none performed better as a base medium than DMEM/F12 when supplemented with a limited amount of FBS (2%) (FIG. 1).

Media Development

Based on the initial results, DMEM/F12 was chosen for use in the original base medium. A continually enriched medium was developed through stepwise addition of individual ingredients, demonstrated to increase the proliferation rates of ASCs. As the list of ingredients lengthened, the serum content could be decreased without sacrificing cell viability and growth, ultimately reaching a level of 0.5% human serum. Specific growth factors were screened multiple times in order to isolate cytokines or hormones that became limiting as the media advanced. Table 1 summarizes this process and the list of ingredients screened at each iteration.

TABLE 1

| Formulation | Modifications Screened | Resulting Base |
|---|---|---|
| AR | N/A | DMEM/F12, L-glutamine, dexamethasone, ascorbic acid 2-phosphate, ITS+3, fatty acid supplement, non-essential amino acids, antibiotic-antimycotic |
| AR2 | AR + (EGF, PDGF, bFGF or gluten peptone) | AR + PDGF + EGF |
| AR3 | AR2 + (bFGF, FLT-3 ligand, HGF, IGF-1, SCGF-β, SDF-1, VEGF, SCF, hydrocortisone, estradiol, progesterone, TNFα, IL-1β or human serum) | AR2 + 0.5% human serum |
| AR4 | AR3 + (bFGF, FLT-3 ligand, HGF, IGF-1, SCGF-β, SDF-1, VEGF, SCF, hydrocortisone, estradiol, progesterone, TNFα or IL-1β) | AR3 + SCGF-β + TNFα |
| AR5 | AR4 + (bFGF, FLT-3 ligand, HGF, IGF-1, SDF-1, VEGF, SCF, hydrocortisone, estradiol, progesterone, IL-1β or TGF-β1) | AR4 + estradiol + progesterone |
| AR6 | AR5 + (bFGF, FLT-3 ligand, HGF, IGF-1, SDF-1, VEGF, SCF, hydrocortisone, IL-1β or TGF-β1) | AR5 + IL-1β + hydrocortisone |
| AR7 | AR6 + (peptones PPA, PPB, WPA, SPA, SPB, YE, UFYE, MER2, MER3, CPN1 or GPN3); substituting ITS for ITS +3, & AR6 at modified concentrations | AR6 at modified concentrations |
| AR8 | AR7 at modified concentrations | see table 2 |

The final recipe, which was tested in the subsequent work, includes the base medium DMEM/F12 supplemented with five growth factors, four hormones, several nutritional supplements, and the optional supplementation with 0.5% human serum (Table 2). Table 2 summarizes studies which started with an initial base recipe, and then modifications were screened individually for their ability to enhance cell proliferation. Those modifications demonstrating a statistically significant increase in proliferation compared with the starting formula were added to a new base recipe. This was repeated in a stepwise fashion leading to the development of a rich basal media. The base medium ingredients of the invention are provided in Table 2, which comprises DMEM/F12 and the ingredients listed in Table 2.

TABLE 2

General Medium Formulations of the Invention

| DMEM/F12 (with glutamine) | |
|---|---|
| AR8 Base Recipe | |
| 0.1 mM | L-glutamine |
| $1 \times 10^{-8}$ M | Dexamethasone |
| 100 μM | Ascorbic acid 2-phosphate (ASAP) |
| 0.50% | ITS+3 |
| 0.05% | Fatty acid supplement |
| 1% | NEAA (non essential amino acids) |
| $1 \times 10^{-8}$ M | Estradiol |
| $1 \times 10^{-8}$ M | Progesterone |
| 500 ng/ml | Hydrocortisone |
| 10 ng/ml | EGF |
| 1 ng/ml | PDGF |
| 1 ng/ml | SCGF-β |
| 1 ng/ml | TNF-α |
| 1 ng/ml | IL-1β |
| 1% | Antibiotic antimycotic |
| 0.5% | Human serum (optional) |
| AR9 substitute ITS+3 of AR8 for: | |
| 1.0 mg/ml | insulin |
| 0.55 mg/ml | human transferrin |
| 0.5 μg/ml | sodium selenite |
| 470 μg/ml | linoleic acid |
| 470 μg/ml | oleic acid |
| 50 mg/ml | human serum albumin |

Briefly, the basic components include: DMEM/F12, antibiotics, nutrients (amino acids, fatty acids, minerals), growth factors, and/or hormones, and or adhesion factors. Several types of albumin were tested.

Preparation of the medium of Table 2 includes the use of: 500 ml of DMEM/F12 (Gibco Cat No. 11320-033; Invitrogen Corp), 250 μl L-glutamine (Gibco Cat No. 25030-081, Invitrogen Corp), 5 ml Antibiotic Antimycotic (Gibco Cat No. 15240-062, Invitrogen Corp), 2.5 ml ITS+3 (Sigma I-2771), 250 μl fatty acid supplement (Sigma F-7050), 5 ml MEM non-essential amino acids (Gibco Cat No. 11140-050, Invitrogen Corp), 50 μM ASAP (Sigma A-8960), 1 ng/ml PDGF-BB (Research Diagnostics Inc., RDI-114b), 10 ng/ml EGF (R & D Systems 236EG), 1 ng/ml SCGF-β (Research Diagnostics Inc. RDI-1022B), 1 ng/ml TNFα (Research Diagnostics Inc., RDI-301), 1 ng/ml IL-1β (Research Diagnostics Inc., RDI-201B), $1 \times 10^{-8}$ M β-estradiol (Sigma E2758-1G), $1 \times 10^{-8}$ M progesterone (Sigma P8783-5G), $1 \times 10^{-8}$ M dexamethasone (Sigma D-8893), and 500 ng/ml hydrocortisone (Sigma H0888-1G). AR9 medium preparation substitutes the ITS+3 of AR8 with the ingredients of the right column of Table 2.

Further preliminary testing of the final base, AR8, as a serum-free medium demonstrated equal subjective attachment rates with and without serum, and did not reveal added benefit with the use of plates coated with collagen type I or type IV, fibronectin, laminin, or poly-D-lysine. Plating density studies were conducted in uncoated plates at 2.0, 5.0, 7.5, 10.0, 15.0, and $20.0 \times 10^{-3}$ cells/cm². Cells plated at $2-7.5 \times 10^{-3}$ cells/cm² ultimately died, while those at higher densities survived and proliferated. Higher density plates were compared to their respective D10 controls. Those cells plated at $15 \times 10^{-3}$ cells/cm² and above subjectively appeared to proliferate at equal rates in standard and serum-free media, while the cells at $10 \times 10^{-3}$ cells/cm² appeared to be inhibited in serum-free media. Based on these early observations, a plating density of $15 \times 10^{-3}$ cells/cm² on uncoated plates was used for testing of serum-free culture.

Proliferation and Maintenance in Culture

Following the development of the AR8 formulation, three fresh cell lines were isolated to investigate cell growth in extended culture in the new media. Each cell line was cultured separately in either serum-free, low serum, or D10 media. Similar fibroblastic morphologies under each culture condition were observed (FIG. 1), although at lower densities, cells in low and serum-free formulations maintained a more compact spindle shaped fibroblastic morphology. Cells cultured under low and serum-free conditions however, tended to grow much more tightly packed as evidenced by their increased cell density at confluent passage, $39 \times 10^{-3}$ cells/cm²* and $24 \times 10^{-3}$ cells/cm²* as compared to $6 \times 10^{-3}$ cells/cm² under standard conditions (*p<0.001). Doubling times averaging 1.86±0.47 and 5.79±2.21 days were found for 0.5% human serum and serum-free media respectively (Table 3).

TABLE 3

Population growth results (n = 3)

|  | ½% Human Serum | Serum Free |
|---|---|---|
| Doubling Time | 1.86 ± 0.47 | 5.79 ± 2.21 |
| Population Doublings | 30.50 ± 3.04 | 1.77 ± 0.80 |
| Days in Culture | 120.67 ± 10.21 | 47.00 ± 9.85 |
| Passages | 10.67 ± 1.15 | 2.67 ± 1.53 |

Differentiation

Following culture in serum-free and low serum media for three passages, cells were tested for adipo-, osteo-, and chondrogenic potential using established differentiation media [19]. Differentiation was confirmed by positive Oil Red O, alizarin red, and alcian blue staining respectively (FIG. 3). FIG. 3 summarizes the multilineage differentiation potential of passage 3 ASCs cultured in serum-free AR8 and in AR8 containing 0.5% human serum. Adipogenic and osteogenic differentiation were further characterized using semi-quantitative colorimetric absorbance assays in comparison to non-differentiated controls (Table 4). Greater differentiation of cells from both low and serum-free culture was found in both lineages. Results were measured by absorbance plate readers following the solubilization of Oil red 0 and Alizarin red stains respectively (*p<0.05).

Serum-free medium may also be used. For example, plating ASCs using micromass culture in AR8 serum-free medium results in the formation of chondrogenic nodules, and the serum-free can also be used for osteogenic differentiation.

TABLE 4

Relative semi-quantitative differentiation results
for adipogenic and osteogenic differentiation.

|  | Oil red O Staining | | Alizarin Staining | |
| --- | --- | --- | --- | --- |
|  | AR8 0.5% | AR8sf | AR8sf | AR8 0.5% |
| Differentiation Media | 1.56 ± 0.85* | 0.32 ± 0.12* | 1.60 ± 0.81* | 0.89 ± 0.56 |
| Non-differentiated Control | 0.43 ± 0.48 | 0.20 ± 0.06 | 0.16 ± 0.13 | 0.66 ± 0.53 |

Flow Cytometry Characterization

In order to further characterize those cell populations obtained under each culture condition, flow cytometry studies were done at each passage as population size allowed (Table 5). Subpopulations positive for the putative stem cell markers CD34 and ALDH were identified under each condition. While significantly fewer CD34+ cells were identified in AR80.5% HS populations when compared to standard culture conditions at passage 2-3 (8.5%±3.3 and 33.3%±6.5), ALDH+ cells were significantly more numerous (29.3%±1.3 and 11.8%±5.5). Expression of CD184, implicated in stem cell homing, and NG2, a marker suggestive of pericytes, were also similar with the exception of decreased NG2 expression in AR8sf cells in early passage. Endothelial cell markers CD31 and CD133 were not present under standard conditions and very low in all other samples. This percentage further diminished to near zero over continued passage. Human cell markers were >98% positive in all groups.

TABLE 5

Summarized flow cytometric characterization of three patient
cell lines each cultured in three media conditions.

|  | D10 | AR8 0.5% | AR8 sf |
| --- | --- | --- | --- |
| | Passage 0-1 | | |
| CD34 | 22.7 ± 18.8 (4) | 5.2 ± 2.5 (4) | 36.4 ± 13.3 (2) |
| ALDH | 15.4 ± 2.1 (4) | 15.2 ± 3.8 (4) | 15.0 ± 2.2 (2) |
| CD184 | 0.3 ± 0.4 (4) | 0.0 ± 0.1 (4) | 0.2 ± 0.3 (2) |
| NG2 | 10.7 ± 4.9 (4) | 6.9 ± 2.6 (4) | 1.2* (1) |
| CD31 | 0.0 ± 0.0 (4) | 2.9 ± 2.0 (4) | 3.5 ± 2.6 (2) |
| CD133 | 0.0 ± 0.0 (4) | 0.1 ± 0.2 (4) | 1.0 ± 0.4 (2) |
| HLA | 98.7 ± 1.1 (4) | 99.4 ± 0.4 (4) | 99.7 ± 0.1 (2) |
| | Passage 2-3 | | |
| CD34 | 33.3 ± 6.5 (6) | 8.5 ± 3.3* (5) | 21.9 ± 11.5 (2) |
| ALDH | 11.8 ± 5.5 (4) | 29.3 ± 1.3* (5) | 13.1 ± 8.8 (2) |
| CD184 | 0.0 (1) | 0.1 ± 0.2 (5) | 0.0 ± 0.0 (2) |
| NG2 | 17.5 ± 18.6 (6) | 19.3 ± 19.5 (5) | 1.7 ± 1.5 (3) |
| CD31 | 0.0 ± 0.0 (4) | 1.0 ± 0.6* (5) | 0.8 ± 0.9 (3) |
| CD133 | 0.1 ± 0.2 (3) | 0.2 ± 0.2 (5) | 0.0 ± 0.0 (3) |
| HLA | 99.3 ± 0.1 (6) | 99.5 ± 0.3 (5) | 98.4 ± 1.0 (3) |
| | Passage 4-5 | | |
| CD34 | 34.6 ± 4.9 (2) | 7.9 ± 3.1 (6) | — |
| ALDH | 19.9 ± 6.8 (2) | 19.0 ± 6.3 (6) | — |
| CD184 | — | 0.0 ± 0.0 (4) | — |
| NG2 | 15.7 ± 9.3 (2) | 7.9 ± 5.8 (6) | — |
| CD31 | 0.0 ± 0.0 (2) | 1.0 ± 1.0 (6) | — |
| CD133 | 0.0 (1) | 0.3 ± 0.4 (4) | — |
| HLA | 99.3 ± 0.0 (2) | 99.6 ± 0.1* (6) | — |

Mean ± SD (n)
*p < 0.05

Serum Lot Screening

Figure 4:
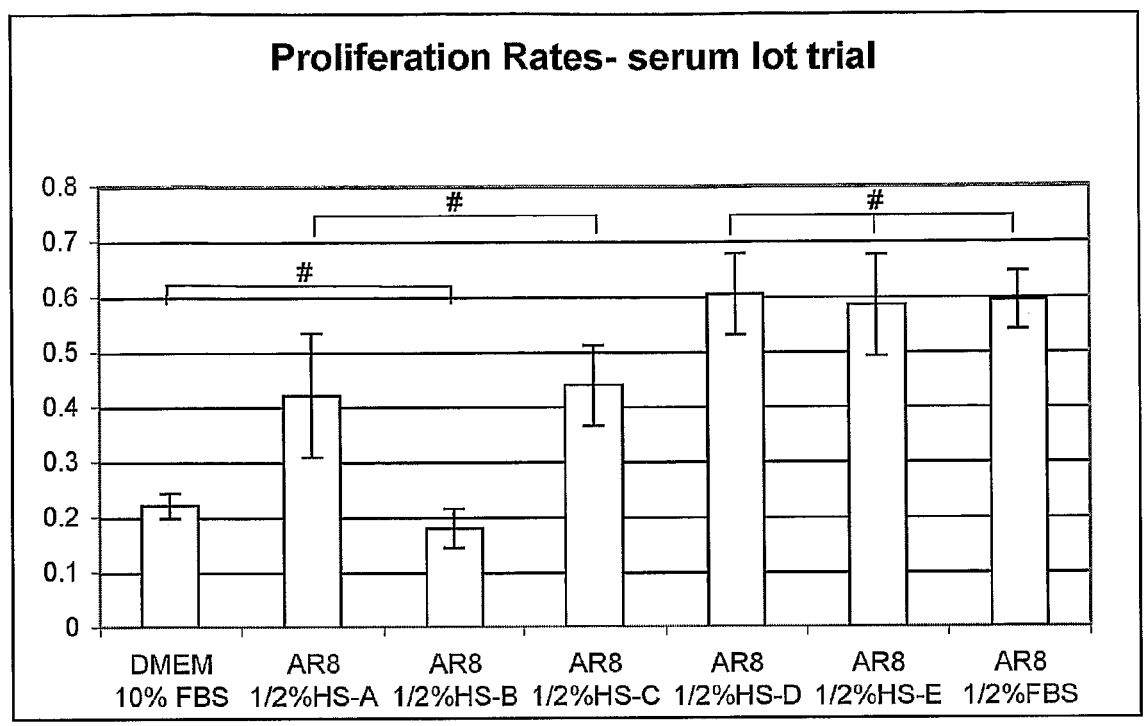
FIG. 4 represents graphically the relative proliferation rates of ASC's after culture in different serum lots for 7 days. Proliferation was measured by an absorbance plate reader using a colorimetric MTS assay. Significant differences (p<0.05) were found between all samples except those noted with a #. The groups included, DMEM with 10% FBS, AR8 with 0.5% HS-A, AR8 with 0.5% HS-B, AR8 with 0.5% HS-C, AR8 with 0.5% HS-D, AR8 with 0.5% HS-E, AR8 with 0.5% FBS.

To assess the potential need for prescreened lots of human serum, MTS proliferation assays were performed on cells grown in AR8+0.5% serum. Five lots of human serum and one lot of FBS were tested, as well as the baseline medium DMEM/F12+10% FBS (see FIG. 4). Significant differences were found between the lots of human serum, however 4 out of 5 lots of human serum used to supplement AR8 0.5% serum demonstrated significantly greater rates of proliferation than the control medium DMEM/F12+10% FBS. No statistically significant difference was found between the final lot of human serum-supplemented AR8 and the control media.

Discussion

The present application discloses enriched media for mesenchymal cell expansion through iterative screening of dozens of factors associated with mesenchymal and or stem cell growth in culture. Multiple protein sources were screened, however albumin contained within the ITS+3 supplement was the only viable source identified. Media formulated without albumin (ITS rather than ITS+3) or with a variety of plant and animal peptone sources did not support growth. Additional amino acids were added to the media, and may have reduced, but did not eliminate the need for albumin. Preliminary results with one cell line have demonstrated successful cell culture using an animal product-free version of the media described herein, formulated with human serum albumin and recombinant human insulin. This formulation has yet to be tested in long-term culture with multiple patient cell lines; however, it is likely that a defined and animal product-free medium could be readily adapted for clinical use.

Proliferation data from three patients has demonstrated successful culture of ASCs in both very low and serum-free media. The addition of 0.5% human serum made an enormous difference in the proliferation rates of cells in culture. This small amount of serum could be easily obtained for autologous use in clinical trials, and could allow for the very rapid and robust expansion of cells. While adipose tissue is frequently available in abundance, potential applications using the patellar fat pad, or perirenal fat necessarily start with a limited supply of tissue. A reliable method for rapid cell expansion in vitro could greatly improve the flexibility of these approaches, particularly where multiple cell applications are desirable. The serum-free culture system disclosed herein did not support a significant proliferative rate, in part due to the high plating densities necessary under these conditions. Frequently, using this culture system, only one half a population doubling was demonstrated before the cells came to confluence and were passaged. While not an ideal method for cell expansion, this media, to the applicant's knowledge, represents the only serum-free system for the maintenance of ASCs over time. When sufficient cell numbers are available, this media can be used to maintain them in culture for several weeks. Researchers interested in fractionating conditioned media may additionally find the defined nature of this system ideal for short-term experiments.

Further characterization of the cell populations cultured in each medium confirmed their multipotentiality along adipo-, osteo-, and chondrogenic lineages. Flow cytometry demonstrated a similar pattern of cell surface marker expression across various culture methods. Noted exceptions included the lower rates of CD 34 expression concurrent with higher rates of ALDH in populations cultured in AR8 0.5% HS. As both are purported to be stem cell markers, the significance of these findings is unclear at this time. As expression of cell markers is a transient phenotype, the true test of these cells will come only with in vivo trials which can directly evaluate their therapeutic potential.

Although significant differences were found between different lots of human serum, all five lots tested were capable of supporting both cell survival and proliferation to a degree at least as great as standard media. It is interesting to note that single donor derived serum lots (C-E) tended to perform better than pooled serum lots (A and B). This may be due to the health or serum composition of particular donors, differences in processing techniques, or simple random chance (p=0.31). It does however seem an important factor to consider in future work.

CONCLUSION

The present application discloses two new media systems for the culture of human ASCs which yield multipotential stem cells. The multipotential cells exhibit a similar cell surface marker expression to cells grown in previously published media containing 10% FBS. The rapid growth rates and higher cell density seen in low serum formulations translate to reduced time, labor, and laboratory space for expansion to a given number of cells. While differences were seen between human serum donor sources, all lots tested herein supported cell growth. The use of fresh autologous serum may well prove more ideal than the processed and frozen serum available commercially. The multipotentiality of these cell populations, in addition to their continued expression of CD34 and ALDH, suggest that cells cultured under these conditions may well retain the regenerative capacity widely observed of ASCs. In vivo trials have yet to test this hypothesis; however, in vitro data suggests that cells grown using these methods may possess all the inherent promise for translational use in the future.

BIBLIOGRAPHY

1 PETERSON B, ZHANG J, IGLESIAS R et al.: Healing of critically sized femoral defects, using genetically modified mesenchymal stem cells from human adipose tissue. Tissue Engineering (2005) 11(1-2):120-129.
2 COWAN C M, SHI Y-Y, AALAMI O O et al.: Adipose-derived adult stromal cells heal critical-size mouse calvarial defects. Nature Biotechnology (2004) 22(5):560-567.
3 LENDECKEL S, JODICKE A, CHRISTOPHIS P et al.: Autologous stem cells (adipose) and fibrin glue used to treat widespread traumatic calvarial defects: case report. Journal of Cranio-Maxillo-Facial Surgery (2004) 32(6): 370-373.
4 GUILAK F, AWAD H A, FERMOR B, LEDDY H A, GIMBLE J M: Adipose-derived adult stem cells for cartilage tissue engineering. Biorheology (2004) 41(3-4):389-399.
5 FRASER J K, SCHREIBER R E, ZUK P A, HEDRICK M H: Adult stem cell therapy for the heart. International Journal of Biochemistry & Cell Biology (2004) 36(4):658-666.
6 PITTENGER M F, MARTIN B J: Mesenchymal stem cells and their potential as cardiac therapeutics. Circulation Research (2004) 95(1):9-20.
7 PLANAT-BENARD V, MENARD C, ANDRE M et al.: Spontaneous cardiomyocyte differentiation from adipose tissue stroma cells. [see comment]. Circulation Research (2004) 94(2) 223-229.
8 KANG S K, LEE D H, BAE Y C et al.: Improvement of neurological deficits by intracerebral transplantation of human adipose tissue-derived stromal cells after cerebral ischemia in rats. [see comment]. Experimental Neurology (2003) 183(2):355-366.
9 CHEN J, LI Y, WANG L et al.: Therapeutic benefit of intravenous administration of bone marrow stromal cells after cerebral ischemia in rats. Stroke (2001) 32(4):1005-1011.
10 SPEES J L, GREGORY C A, SINGH H et al.: Internalized antigens must be removed to prepare hypoimmunogenic mesenchymal stem cells for cell and gene therapy. Molecular Therapy: the Journal of the American Society of Gene Therapy (2004) 9(5):747-756.
11 MACKENSEN A, DRAGER R, SCHLESIER M, MERTELSMANN R, LINDEMANN A: Presence of IgE antibodies to bovine serum albumin in a patient developing anaphylaxis after vaccination with human peptide-pulsed dendritic cells. Cancer Immunology, Immunotherapy (2000) 49(3):152-156.
12 SELVAGGI T A, WALKER R E, FLEISHER T A: Development of antibodies to fetal calf serum with arthus-like reactions in human immunodeficiency virus-infected patients given syngeneic lymphocyte infusions. Blood (1997) 89(3):776-779.
13 TUSCHONG L, SOENEN S L, BLAESE R M, CANDOTTI F, MUUL L M: Immune response to fetal calf serum by two adenosine deaminase-deficient patients after T cell gene therapy. Human Gene Therapy (2002) 13(13): 1605-1610.
14 KIM S J, CHO H H, KIM Y J et al.: Human adipose stromal cells expanded in human serum promote engraftment of human peripheral blood hematopoietic stem cells in NOD/SCID mice. Biochemical & Biophysical Research Communications (2005) 329(1):25-31.
15 ZUK P A, ZHU M, MIZUNO H et al.: Multilineage cells from human adipose tissue: implications for cell-based therapies. Tissue Engineering (2001) 7(2):211-228.
16 KATZ A J: Mesenchymal cell culture: adipose tissue. In Methods of Tissue Engineering. Atala A et al. (eds) Academic Press, San Diego (2002): 277-286.
17 RAMIREZ-ZACARIAS J L, CASTRO-MUNOZLEDO F, KURI-HARCUCH W: Quantitation of adipose conversion and triglycerides by staining intracytoplasmic lipids with Oil red O. Histochemistry (1992) 97(6):493-497.
18 HUANG J I, ZUK P A, JONES N F et al.: Chondrogenic potential of multipotential cells from human adipose tissue. Plastic & Reconstructive Surgery (2004) 113(2):585-594.
19 ZUK P A, ZHU M, ASHJIAN P et al.: Human adipose tissue is a source of multipotent stem cells. Molecular Biology of the Cell (2002) 13(12):4279-4295.

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein. The appended claims are intended to be construed to include all such embodiments and equivalent variations.

What is claimed is:

1. A serum-free medium or a medium enriched with about 0.5% serum, said medium comprising a basal medium, growth factors comprising platelet-derived growth factor subunit B (PDGF-BB), epidermal growth factor (EGF), stem cell growth factor-β (SCGF-β), tumor necrosis factor alpha (TNFα), and interleukin-1 beta (IL-1β) and additional ingredients, wherein adipose tissue-derived stem cells cultured in said medium retain the ability to differentiate.

2. The medium of claim 1, wherein said medium comprises the basal medium Dulbecco's modified Eagle's medium (DMEM)/F12 (DMEM/F12).

3. The medium of claim 2, wherein said medium comprises at least one ingredient selected from the group consisting of L-glutamine, antibiotic, antimycotic, insulin, transferrin, selenium, a fatty acid supplement, non-essential amino acids, ascorbic acid 2-phosphate (ASAP), β-estradiol, progesterone, dexamethasone, and hydrocortisone.

4. The medium of claim 1, wherein said media comprises a serum concentration of about 0.5%.

5. A method of culturing adipose tissue-derived stem cells comprising obtaining adipose tissue-derived stem cells, seeding said cells into a tissue culture dish or plate, contacting said cells with said medium of claim 1, thereby culturing adipose tissue-derived stem cells, wherein said cells retain the ability to differentiate.

6. The method of claim 5, wherein said cells proliferate in culture.

7. The method of claim 6, wherein said cell is a human cell.

8. The method of claim 5, wherein said cells can differentiate into cells selected from the group consisting of adipocytes, chondrocytes, and osteoblasts, or precursors thereof.

9. The method of claim 5, wherein said medium comprises the basal medium DMEM/F12.

10. The method of claim 9, wherein said medium further comprises at least one ingredient selected from the group consisting of L-glutamine, antibiotic, antimycotic, insulin, transferrin, selenium, a fatty acid supplement, nonessential amino acids, ASAP, β-estradiol, progesterone, dexamethasone, and hydrocortisone.

11. The method of claim 5, wherein said cells are grown with the use of feeder cells.

12. The method of claim 5, wherein said tissue culture dish or plate is pretreated to enhance cell attachment.

13. The method of claim 12 wherein said tissue culture dish or plate is pretreated to enhance cell attachment by coating with at least one molecule selected from the group consisting of collagen, fibronectin, and albumin.

14. The method of claim 5, wherein said cells can be serially passaged.

15. The method of claim 5, wherein said medium comprises up to about 0.5% serum.

16. The method of claim 15, wherein said serum is human serum.

17. A medium comprising about 500 ml DMEM/F12, 250 μl L-glutamine, 5 ml antibiotic antimycotic, 2.5 ml insulin/transferrin/selenium (ITS+3), 250 μl fatty acid supplement, 5 ml minimum essential medium (MEM) non-essential amino acids, 50 μM ASAP, 1 ng/ml PDGF-BB, 10 ng/ml EGF, 1 ng/ml SCGF-β, 1 ng/ml TNFα, 1 ng/ml IL-1β, $1\times10^{-8}$ β-estradiol, $1\times10^{-8}$, progesterone, $1\times10^{-8}$ dexamethasone, and 500 ng/ml hydrocortisone.

* * * * *